United States Patent [19]

Berry, Jr.

[11] Patent Number: 4,762,688

[45] Date of Patent: Aug. 9, 1988

[54] AUTOCLAVE TRAY FOR SURGICAL APPARATUS

[76] Inventor: Bernie B. Berry, Jr., 5315 E. Pleasant Run Pkwy., S. Dr., Indianapolis, Ind. 46219

[21] Appl. No.: 49,027

[22] Filed: May 13, 1987

Related U.S. Application Data

[63] Continuation of Ser. No. 921,888, Oct. 26, 1988, abandoned, which is a continuation of Ser. No. 819,205, Jan. 15, 1986, abandoned, which is a continuation-in-part of Ser. No. 579,022, Feb. 10, 1984, abandoned.

[51] Int. Cl.⁴ .................. A61L 2/00; A61L 31/00; B65D 81/18
[52] U.S. Cl. .................. 422/310; 422/297; 422/300; 206/363; 206/365; 206/368; 206/370; 206/349; 206/493; 211/41; 211/88; 211/89
[58] Field of Search ............ 422/297, 300, 310; 211/13, 41, 60.1, 70.6, 69, 86, 88, 89; 206/363, 365, 368, 370, 349, 493

[56] References Cited

U.S. PATENT DOCUMENTS

| | | | |
|---|---|---|---|
| 144,539 | 11/1873 | Hayes | 211/69 |
| 354,799 | 12/1886 | McConahy . | |
| 1,246,536 | 11/1917 | Baistol | 211/69 |
| 1,761,382 | 6/1930 | Alcalis | 211/70.7 |
| 2,472,028 | 5/1949 | Son | 422/310 |
| 2,659,485 | 11/1953 | Duley et al. | 211/69 X |
| 2,974,804 | 3/1961 | Mano | 211/70.6 |
| 3,712,465 | 1/1973 | Deuschle | 211/60.1 X |
| 4,043,754 | 8/1977 | Sklar | 211/70.6 X |
| 4,135,868 | 1/1979 | Schainholz | 422/300 X |
| 4,153,160 | 5/1979 | Leigh | 206/370 |
| 4,219,178 | 8/1980 | Assion | 211/89 X |
| 4,262,799 | 4/1981 | Perrett | 422/300 X |
| 4,353,694 | 10/1982 | Peterin | 206/370 X |
| 4,457,327 | 7/1984 | Pepper | 422/114 X |
| 4,541,992 | 9/1985 | Jerge et al. | 422/300 |

Primary Examiner—Barry S. Richman
Assistant Examiner—Lynn M. Kummert
Attorney, Agent, or Firm—Shlesinger, Arkwright, Garvey

[57] ABSTRACT

An autoclave tray for sterilization of surgical components and equipment includes slotted, polysulfone holders each having a base portion, a body portion and a connecting portion wherein the connecting portion is narrower than both the base portion and the body portion, the body portion being designed to receive and hold at least one surgical component, a tray arranged with oblong slots for receiving and holding one or more synthetic holders wherein the oblong slots include a narrow channel portion and an enlarged keyhole portion. The holders may be positioned in the oblong slots by passing the leading edge of the base portion through the enlarged keyhole portion of the slot and sliding the connecting portion along and within the narrow channel portion. The tray further includes a plurality of steam holes disposed about the surface of the tray. The body portion of the holder includes a pair of parallel and vertically extending receiving slots wherein each slot is similarly configured with a pair of spaced-apart cylindrical clearance areas and a narrower connecting channel open at its uppermost extreme and connecting the uppermost edge of the receiving portion with the two cylindrical clearance areas. Each cylindrical clearance area is suitably designed to receive and retain a portion of a surgical component wherein receipt of two such surgical components by the same vertical slot is performed in such a manner that neither component is able to contact the other.

19 Claims, 4 Drawing Sheets

AUTOCLAVE TRAY FOR SURGICAL APPARATUS

CROSS REFERENCE TO RELATED APPLICATIONS

This is a continuation of Ser. No. 921,888 filed Oct. 26, 1988, which is in turn a continuation of Ser. No. 819,205 filed Jan. 15, 1986, which is in turn a continuation-in-part of Ser. No. 579,022 filed Feb. 10, 1984, all of which are now abandoned.

BACKGROUND OF THE INVENTION

The present invention relates in general to surgical trays and means to retain surgical instruments and related apparata on such trays. More particularly, the present invention relates to an autoclave tray wherein implanting tools and prosthetic members may be securely retained in a quiet and safe manner through all phases of autoclaving for sterilization of the tools and members.

One preliminary step to any surgical procedure is to have the surgical instruments and related components and accessories properly sterilized. This procedure involves subjecting the various parts and components to an autoclaving operation wherein these objects are subjected to an elevated temperature in the range of 270 degrees Fahrenheit and an elevated pressure. Prior to the autoclaving operation, the holder for the tools, instruments and components is turned or rotated as they are wrapped.

As should be understood, one requirement for the tray and holders for these instruments and components is that they be able to withstand the elevated temperatures and pressures and to do so for many cycles. Any tray and instrument holder which would become unsuitable for continued use after only a few autoclaving cycles represents a design inefficiency not only from the standpoint of cost but as well from the standpoint of inventory control and the time and inconvenience associated with having to constantly replace a damaged or otherwise unsuitable autoclaving tray.

As might be expected, the surgical instruments, devices and prosthetic components which must be sterilized before an operation are mounted onto an autoclaving tray and supported on the tray by means of retainers. Due to the elevated temperature and pressures, these trays and holders have traditionally always been constructed of some metal or metal alloy. Clearly, metal has been found to be a suitable material that can be subjected to numerous cycles of the autoclaving operation without showing signs of wear or damage. With the material selection problem solved, designers of autoclaving trays then turned to another concern. This other concern was how to configure the tray so that any tray could receive a variety of instruments and prosthetic components or similar items to be autoclaved when the requirements and component mix were not always the same. Not only would the types of instruments and components change, but the number of such components might be different for any surgical procedure and parts secured from different manufacturers might be sized slightly differently. As these differences would arise, not only would the autoclaving tray require some change or modification, but the design of the holders for the various instruments and components might also need to change or be designed in some manner so as to be variable and thus adaptable to various sizes and shapes.

One approach to the foregoing problem was to design what could be referred to as "universal" autoclaving trays and holders which were configured on the basis of a matrix screen having a uniformly spaced pattern of holder-receiving holes extending throughout the surface of the screen. By configuring the instrument holders of a diameter size to fit within the various matrix holes in the screen, it was possible to configure an autoclaving tray which could receive various-styled instruments in a variety of orientations and configurations. An example of this type of device is offered by the Sklar patent reference, U.S. Pat. No. 4,043,754 which issued Aug. 23, 1977. This reference focuses primarily on the design of a U-shaped pin for a sterilizing tray in order to hold surgical instruments during sterilization. The concept of Sklar relies primarily on a minimal push-in fit of the U-shaped pins into the various holes of the perforated metal bottom surface of the tray. One problem though is that this particular style of device does not offer a secure means of retaining surgical instruments as the tray may be turned or rotated so as to insure thorough sterilization. Even if the pins could be retained in the perforated metal surface during such turning and rotating procedures, very likely the instruments held by the pins would move about due to the height of the interior clearance within the U-shape relative to the location of the abutment stops on the pin which fix the vertical height of the pin above the perforated metal surface. While this increased vertical height within the U-shaped pin might be suitable for retaining more than one identical surgical instrument, such instruments would no doubt bang against each other during the turning and rotating of the wrapping procedure, and scratch or mar the respective surfaces. A great deal of noise would also be created by this movement and if critical prosthetic components were mounted, there would be a significant risk that precisely machined surfaces might come in contact with one another thereby dulling or nicking these critically machined surfaces or edges.

A somewhat related disclosure is found in the patent reference issued to Schainholz, U.S. Pat. No. 4,135,868 which issued Jan. 23, 1979. This particular patent reference discloses another perforated metal surface which allows the instrument holders to be inserted and arranged in an infinite variety of orientations and configurations. The holders themselves have a variety of shapes and sizes but are installed by means of push-in pins or buttons disposed along the bottom or lower surface of the respective holder. One concern of this particular design as previously addressed with the Sklar reference is the fact that turning and inverting during an autoclaving operation of only support surface 26 would cause the instruments to fall out of their respective holders or the holders to fall out of the perforated metal surface. To attempt to correct this design deficiency, the Schainholz patent discloses a top surface formed as part of a receptacle or box which is fitted with clamping pads or blocks. When the lid is closed over the bottom retaining surface which holds the surgical instruments, a plurality of rectangular blocks of heat resistant material of a rubber-like compound clamp against the various tools and instruments and hold them in position during the autoclaving operation.

What this design necessitates and one of the reasons why it is felt to be a significant disadvantage is that both a top and a bottom surface are required and must be held together by some type of receptacle or box construction. Further, one pair of holders for any particular surgical instrument is insufficient and there must be provided an additional pair of holders and the compressing rubber-like material pad in order to hold the instrument in place. As a result, not only is there a large number of pieces to arrange on the respective perforated metal surfaces, but these various items must be aligned with one another so that the rubber-like material pads properly compress the tools which are held in the lower surface by the various holders.

A further concern with this particular design is that two or more identical prosthetic implant components or surgical instruments cannot be stacked on top of each other due in part to the shallowness of the lower surface holders as well as due to the presence of the compressing pads as part of the upper surface. If such a stacked retention was attempted, the two instruments would be pushed into contact with each other resulting in the aforementioned problems of scratching, denting or marring which not only affects the appearance of the tools or instruments, but which would have a significant degrading effect on precisely cut and machined edges of the prosthetic implant components.

A third reference of which the inventor is aware, although one which is believed to have very limited relevancy to the present invention is the patent issued to McConahy, U.S. Pat. No. 354,799 which issued Dec. 21, 1886. This patent reference discloses a holder for rings, and its only relevancy to the present invention is believed to be in the fact that a variable holding apparatus is disclosed which appears to be capable of receiving variously sized and shaped components.

One very clear problem with the autoclaving apparata of both Sklar and Schainholz is the fact that what is disclosed is not considered to be a conventional and typically styled autoclaving tray. It is important in the design of such trays that their length and width dimensions be suitable not only for the autoclaving procedure, but for placement on an operating or surgical table in a secure and space-efficient manner. The overall height of the tray is also of some concern with regard to the autoclaving equipment and thus designs such as Sklar which may present an unusually high pin member would not be suitable. Similarly, the design of Schainholz would not be suitable, not only from the standpoint that its structure is unsuitable for conventional autoclaving equipment due to its size and cumbersome nature, but that it is as well unsuitable for placement in a surgical operating room because of its top lid and the surface area it occupies when opened.

A related problem with autoclaving trays of the universal design is that there is no uniformity or consistency of component part or surgical tool placement. Due to the number of hospital personnel which may be involved in securing the various components to be autoclaved, loading these components onto an autoclaving tray and then moving the components and tray into the surgical arena, there are numerous chances for errors or omissions. For example, since the universal autoclaving tray has no indication of what should be installed on it or where these items should be installed, every autoclaving cycle even of the same group of components may be arranged differently. If the autoclaving tray is then moved directly into the surgical arena, the operating room personnel will always be looking in a different location to try and find the components or instruments which they must use next. There is also some concern that for any one surgical procedure, such as a total hip or total knee replacement, all of the necessary components may not be provided.

The inventor is aware of an effort to alleviate this problem by configuring an autoclaving tray which is suitable to be transferred from the autoclaving operation directly into the surgical operating room. This tray includes a series of metal brackets which are riveted to the surface of the tray in fixed locations in order to retain a fixed group of surgical instruments and prosthetic implant components. This allows the autoclaving personnel as well as the surgical room personnel to quickly and easily identify not only what components must go where for the autoclaving, but enables the selection of those components quickly and easily once in the operating room. The top surface of the autoclaving tray is configured with instrument outline markings and component part identifications so that hospital personnel, regardless of their position in the cycle or their responsibility, will know what items should go on the tray and where these items should be placed. This allows tray after tray to be identically loaded and contain the proper complement of instruments and prosthetic implant component parts for any surgical procedure.

One concern with this type of device is the expense and time involved to rivet each of the metal brackets onto the autoclaving tray and the inability of a physician or surgeon to modify the tray by changing either the location or style of holders. A further problem with this particular device is that the holders are not capable of holding a plurality of identical components at the same location without them nicking, scratching or marring each other and deteriorating critically machined surfaces, a problem previously discussed. A still further problem with this particular style of autoclaving tray and holder is that the prosthetic component parts and surgical instruments, whether stacked singularly or in combination, will clatter and bang against the respective metal holders during any turning, moving or rotation of the tray and its contents during the wrapping procedure prior to autoclaving.

Each of the foregoing problems, shortcomings and disadvantages of what are believed to be the full range of prior devices are completely solved by the present invention. What the present invention offers is an autoclaving tray with fixed slots arranged throughout the top surface of the tray for receiving in a variety of locations synthetic material holders, wherein the tray contains screened-on markings of the outlines of the instruments and the prosthetic component parts, and the part numbers or similar nomenclature markings. The synthetic holders are designed such that they may either be manually snapped into respective slots which are disposed throughout the surface, or slidably inserted into the slots by means of an enlarged keyhole opening at one end of the slot. When the snap-in approach is used, the holders cannot be removed without partially or totally destroying the particular holder. With the slide-in approach, the holders are removable thereby allowing a holder to be removed, modified or reworked and then reinserted.

Each pin or screw holder is designed so as to retain two or more identical component parts without these parts coming in contact with one another. The particular holders may also be modified by the physician so as to accept a special or modified instrument, and the holders have a scratch-free, mar-free and quiet surface such that there is no damage to the components regardless of the movement of the tray during autoclaving and subsequent use in surgery, even if fully loaded with components. The tray is free of any top lid or upper clamping means thus relying solely on the shape and fit of the synthetic holders for retention of the pins, components and instruments which must be autoclaved. Once the autoclaving procedure is completed, the tray, holders and instruments may be moved directly into the operating room arena at which time the instruments and prosthetic component members may be removed as required by operating room personnel. It is readily apparent, from a visual inspection of the tray, whether or not all necessary components are present and properly located in accordance with the outline shape and corresponding nomenclature. A complete understanding of the present invention as well as the various benefits and improvements which it offers will be presented more fully by the descriptions which follow.

SUMMARY OF THE INVENTION

According to one embodiment of the present invention, there is disclosed an autoclave tray for sterilization of surgical components and equipment which includes a metal tray arranged with a plurality of oblong slots and steam holes and a plurality of slotted, synthetic holders which securely slide into position in the oblong slots wherein the holders include a base portion disposed below the metal tray and a retention portion disposed above the metal tray and arranged with a clearance void and a narrower-width passage connecting the uppermost edge of the retention portion with the clearance void wherein the holder is suitably designed to receive and retain in the clearance void a portion of a surgical component.

One object of the present invention is to provide an improved surgical component holder as part of an improved autoclave tray.

Related objects and advantages of the present invention will be apparent from the following description.

DESCRIPTION OF THE PREFERRED EMBODIMENT

Figure 1:
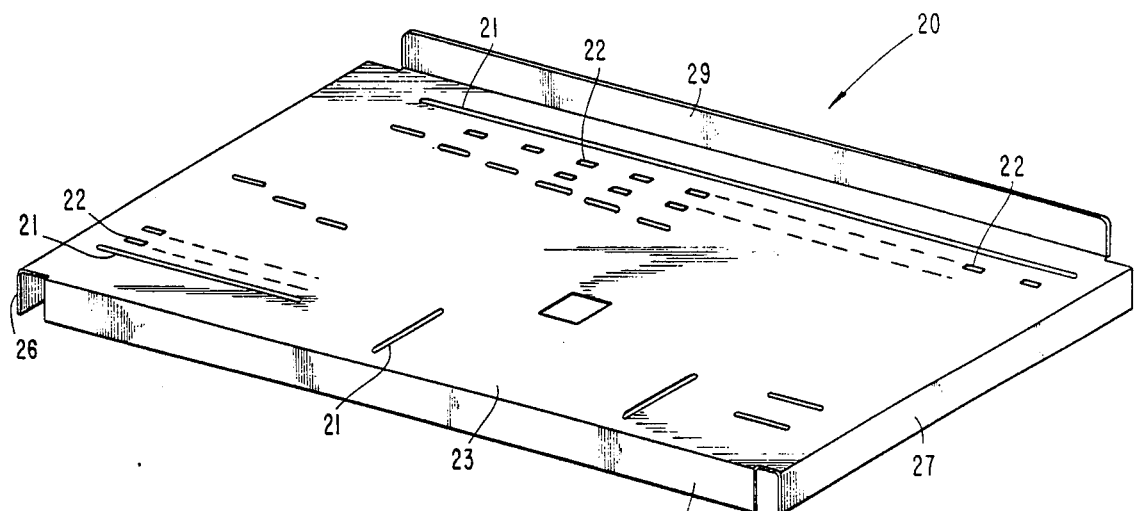
FIG. 1 is a perspective view of an autoclaving tray according to a typical embodiment of the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 8:
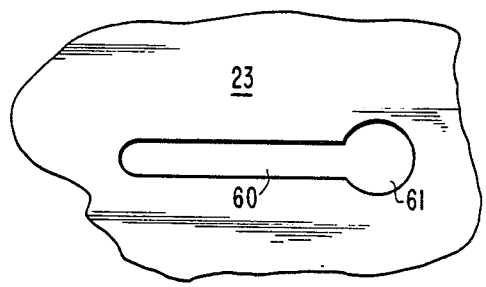
FIG. 8 is a top plan view of a representative, alternative slot design showing an enlarged keyhole end for slidable receipt of holders.

Referring to FIG. 1, there is illustrated a metal autoclave tray 20 which includes a plurality of oblong slots 21 and plurality of rectangular steam holes 22 which are disposed throughout top surface 23. As should be understood and as described in greater detail relative to FIG. 2, the various oblong slots are accurately located and arranged throughout the top surface so as to coincide with holding positions for a preselected combination of prosthetic implant members and surgical instruments. The number and location of the slots are selected so as to retain the necessary complement of components for a particular surgical procedure, such as a total hip or total knee replacement. As should also be understood, the FIG. 1 illustration is intended to convey more of an understanding of the general shape and construction of the tray rather than fully detailing each of the slots and holes and each of the corresponding components and instruments. In this regard, only a partial assortment of slots and holes is provided for illustrative purposes in FIG. 1. Further, the alternative slot style of FIG. 8 is not illustrated in FIG. 1 nor in FIG. 2, though the ability to slide the holders in place, which is enabled by the FIG. 8 slot design, is an important aspect of the present invention. The full detail of tray 20 is presented in FIG. 2 which is a top plan view showing each of the oblong slots and steam holes.

Metal autoclave tray 20 is of a sheet metal construction having three downwardly formed lips, lip 26 on the left side, lip 27 on the right side, and lip 28 in front. The rear portion of the top surface is bent upwardly so as to form rear surface 29. This particular arrangement of bent edges provides a very durable and rigid member which is essentially free of any flexibility or oil-canning effects. The lack of any oil-canning is aided by the overall thickness of the material which is a 3/32 thick anodized aluminum alloy. As illustrated, tray 20 is free of any hinged lid or top portion which could provide a means to clamp components in place. Consequently, as will be described, it is the design and fit of the installed holders which are solely responsible for the retention of the components and instruments to be autoclaved.

Figure 3:
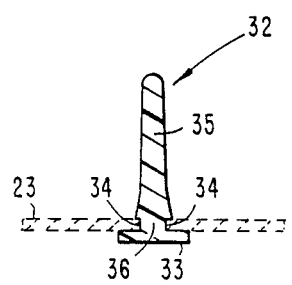
FIG. 3 is a side elevation view in full section of a typical holder as retained in the top surface of the FIG. 1 autoclaving tray.
Figure 4:
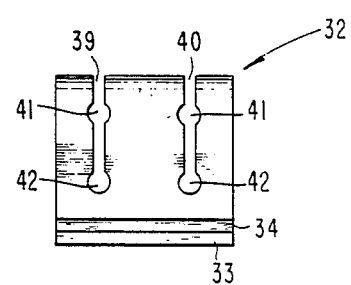
FIG. 4 is a front elevation view of the FIG. 3 holder.
Figure 5:
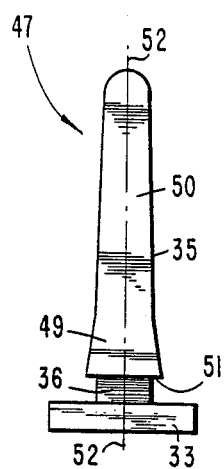
FIG. 5 is an enlarged detail view of the FIG. 3 holder as removed from the FIG. 1 autoclaving tray.
Figure 6:
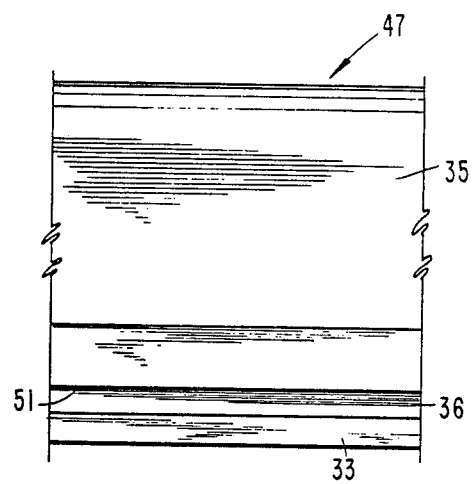
FIG. 6 is a front elevation view of the extrusion which is used to create the various holders for use with the FIG. 1 autoclave tray.

As should be understood and as will be described in greater detail hereinafter, the various oblong slots are properly sized and configured so as to receive one or more compatibly styled holders. The holders are illustrated in FIGS. 3, 4 and 5 and the extrusion which is formed as a starting point for each holder is illustrated in FIG. 6. These holders are positioned within the various oblong slots 21 so as to suitably retain the various prosthetic implant members as well as the implanting tools and related surgical instruments. The various rectangular steam holes 22 disposed in the top surface 23 permit the autoclaving steam to pass freely from one side of the autoclaving tray to the other so as to thoroughly cover each and every portion of the surface of each component part and instrument loaded on the particular tray. The number of these rectangular holes disposed between corresponding oblong slots depends in part on the distance between the oblong slots and the general shape of the instruments which are mounted on the top surface of the tray.

Figure 2:
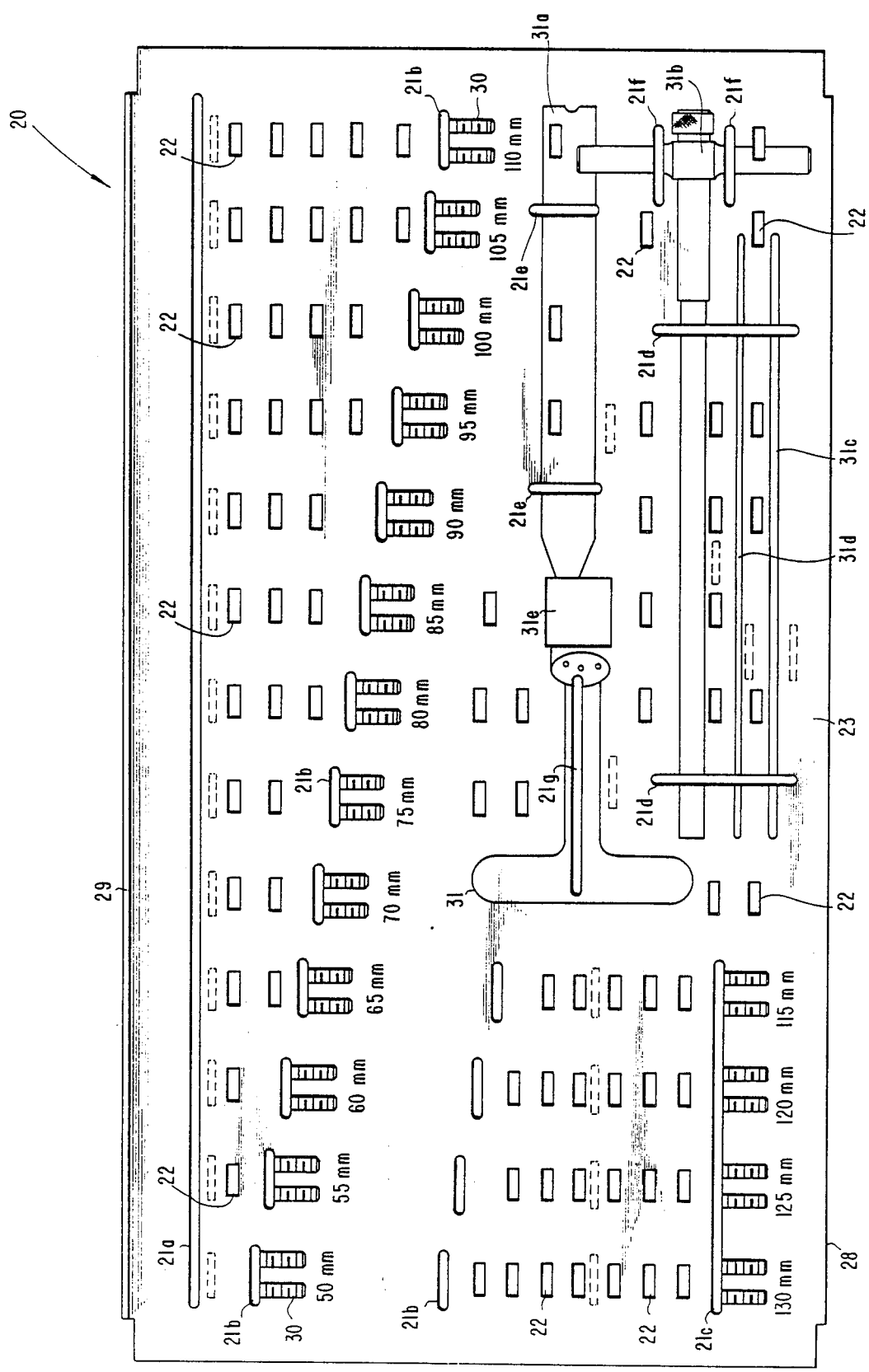
FIG. 2 is a top plan view of the FIG. 1 autoclaving tray detailing each of the instrument holder slots and component outlines.

Referring to FIG. 2, the layout of the top surface 23 of autoclave tray 20 is illustrated in greater detail. Although reference numeral 21 has previously been used for the various oblong slots disposed in the top surface of tray 20, letter suffixes will now be used in combination with reference numeral 21 so as to denote different length slots at different locations within top surface 23.

Spaced inwardly from rear surface 29 is a first oblong slot 21a which extends virtually the entire length of autoclave tray 20 and is configured to receive one or more holders which are internally contoured to receive prosthetic implant screws. Due to the fact that the holder begins as a single, unitary member formed by extruding, it is possible to provide a single holder for the full length of slot 21a or to provide a plurality of shorter-length holders at any location along slot 21a depending upon which particular length prosthetic implant screws are going to be loaded onto the autoclave tray. If a full complement of screws of all of the various lengths are to be provided, then it is necessary to have a corresponding holder at each position along oblong slot 21a.

The corresponding holders that cooperate with the holders installed in slot 21a are positioned in slots 21b. Each slot 21b is of the same longitudinal length and lateral width but are placed in a staggered configuration from the left end to the right end of the top surface. The point to note with regard to slots 21b is that they are virtually identical in all respects and are suitably configured to retain identical holders. The only difference between these various oblong slots 21b is their spatial relationship to slot 21a. As we move from the left side of autoclave tray 20 to the right side, each successive oblong slot 21b moves closer to the front lip 28 and thus farther away from slot 21a. Across the full length of the autoclave tray's top surface there are a total of 13 oblong slots 21b at this location. Each of these slots corresponds to a particular prosthetic implant screw length beginning with the length of 50 mm and going up to a length of 110 mm in uniform 5 mm increments. Consequently, the stagger or length variance between each adjacent oblong slot 21b is the same.

Since each holder, as will be described in greater detail hereinafter, is configured with component-receiving channels disposed in their interior portion (see FIG. 4), it should be understood that these interior channels are properly configured to retain corresponding surgical implant pins or cannulated screws. Each holder which is placed in its corresponding slot 21b is configured with two such internal channels and thus the ink screening on the top surface of the autoclave tray denotes the outline 30 of the distal ends of two prosthetic implant screws. Corresponding actual screws (or pins) are capable of being positioned in each holder at each of these 13 locations. As will also be understood, the vertical height of each holder is sufficient so as to retain two such screws (or pins) in each of the two internal channels for a total of four screws of each predetermined screw length.

The rectangular steam holes 22 which are disposed between slots 21b and slot 21a may be somewhat arbitrary as to number and spacing, beginning with one such rectangular hole for the 55 and 60 mm pins and then increasing to two holes for the next three pin lengths and then after that three holes for the next three lengths, and then four holes for the next two lengths and finally five holes for the final two lengths. There is no rectangular hole provided for the 50 mm pin. Again, the rationale as to the size, spacing and number of such rectangular holes is for the purposes of providing adequate autoclaving fluid in and around all of the component parts and instruments so as to insure complete and thorough sterilization. Due to standardized punch sizes, all steam holes 22 are similarly sized and shaped.

Referring now to the lower left-hand portion of top surface 23, additional surgical screws (or pins) are indicated as being held at that location. In this particular arrangement, a continuous oblong slot 21c is disposed toward the front lip 28 with the individual, segmented and staggered slots 21b being located more interiorly. The stagger is in a reverse direction from what was disclosed for the first series of pins and this selection has been made simply to balance out the pin arrangements so that the longest pins of this second group are in alignment with the shorter pins of the first group. Consequently, the left edge of top surface 23 begins with prosthetic implant pins having a length of 130 mm and then going down to 125, 120 and finally 115 mm as we move inwardly from the left edge of the tray. The 130 mm pin position coincides with the 50 mm pin position and similar alignment is maintained with the other pins moving from left to right. Due to the increased pin lengths retained at this location on the autoclave tray, there are five rectangular steam holes 22 disposed between the cooperating slots for the 115 mm pins and from there going up to six rectangular holes for the next two pin lengths and finally seven rectangular holes for the 130 mm pin.

Finally, additional slots 21d, 21e, 21f and 21g are provided for the retention of holders which in turn receive and retain five implant instruments and accessories. These five implements are identified by their ink-screened shapes which include a drill guide 31, scale 31a, wrench 31b, larger-diameter 9-inch pin 31c and smaller-diameter 9-inch pin 31d. Square cut-out 31e receives the nose of the drill guide which is arranged at a 45-degree angle from the wire handle. The holder received by slot 21g is of a width that is suitable for the wire handle to fit over with a snug fit. In this one instance receiving slots in the holder are not required.

As is illustrated in FIG. 2, each location where either prosthetic implant pins or surgical instruments are held are properly identified with appropriate part number nomenclature and at least a partial outline of the item to be installed at that location. This enables not only proper loading of the autoclave tray and proper identification of the components being selected, but is helpful for reordering parts from inventory. For the purposes of drawing clarity, broken line boxes have been illustrated to denote the location for the part number marking. Each of the component outlines and markings are provided across top surface 23 by silk screening and the ink used is suitable to withstand the temperature and pressure cyclings of repeated autoclaving operations.

Referring to FIG. 3, there is illustrated one holder 32, in a side elevation view, as snapped in place on the top surface 23 of the autoclaving tray. As is to be understood, each holder is similarly styled as to its side elevation appearance due to the fact that they all begin as an identical extruded member. The extruded shape of holder 32 includes a base portion 33, a pair of oppositely disposed snap-in, receiving notches 34 and a body portion 35 which extends upwardly from the top surface 23, the lower section or base of which is tapered. The lower surface of body portion 35 abuts directly against top surface 23 and when in this abutting configuration, the two receiving notches receive corresponding inside slot edges of the top surface. The base portion 33 is substantially wider than the maximum width of the lower surface of the tapered retention portion. Disposed between the lower edge of the body portion and the base portion 33 is an integral connecting portion 36 which additionally defines the innermost surface of each receiving notch. Connecting portion 36 is that part of holder 32 which is received within the various oblong slots of top surface 23. Due to the width of the lower surface of the tapered base of body portion 35, which is only slightly wider than the width of the slot into which it is installed, the holder may be installed by first inserting the tip of the retention portion from the back side of top surface 23 through a corresponding oblong slot and then snapping the holder into position. This manual insertion method does not require any tools or other modications due to the dimensional accuracy of the extruded holders 32 and the compatible dimensional accuracy of the various oblong slots. Due to the extruded nature of holder 32, portion 36 and base portion 33 each have substantially rectangular lateral and longitudinal cross sections throughout their entirety.

One advantage of the tapered configuration of the base of body portion 35 and the design of its lower edge which abuts against top surface 23 is the fact that any downward force which would attempt to push the respective holder out of its retained position within the oblong slot results primarily in bending of the body portion which absorbs the majority of the force precluding a sufficient force generation to push the holder out. If the member is clamped so as to preclude such bending while force is applied to push the holders out, the generally triangular shape of the base of body portion 35 enables it to expand outwardly in response to the compression thereby virtually guaranteeing the inability to manually remove any of the holders by such application of force.

Each holder is constructed of polysulfone, enabling it to be flexible and machinable yet extremely durable and certainly the ideal material for this present application. From the standpoint of the machinability of this particular material, it is to be understood that the body portion 35 may be easily configured to correspond to the various components to be held. It is also possible due to this machinability that the holders may be cut by a knife or similar sharp instrument allowing the physician or assistant to cut them to a specific and specialized shape which may be required in the event a specialized instrument or prosthetic member is required for a particular surgical procedure.

Referring to FIG. 4, a typical machined configuration for holder 32 is illustrated. This front elevation view of holder 32 indicates that two receiving channels or slots 39 and 40 have been configured in body portion 35. Each receiving slot has a pair of circular areas 41 and 42 which are provided for the retention of prosthetic implant screws (or pins). As should be understood, with a pair of holders 32 properly spaced and aligned with one another in a pair of corresponding, parallel oblong slots (previously disclosed), a first pair of prosthetic implant screws may be pushed downwardly into the two holders, with one screw being inserted into each of the receiving slots 39 of each holder, and the other screw being inserted into the other receiving slots 40. These screws are pushed downwardly until they are positioned within corresponding circular areas 42. Due to the fact that the diameter of the circular areas 42 and 41 is greater than the dimensional width of the receiving slots, some deflection and flexibility is required in order to pass the respective screws through the narrower regions of the receiving slots until they come to rest in the larger sized circular areas. What this dimensional arrangement permits is a second pair of screws to be inserted and retained in circular areas 41.

Figure 7:
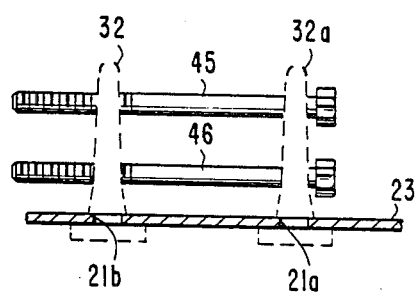
FIG. 7 is a side elevation view of two surgical screws as retained in a stacked arrangement within two holders which are secured within the top surface of the FIG. 1 autoclave tray.

This stacked arrangement of two surgical screws which remain spaced apart from one another and securely retained is of significant importance in that not only may a larger number of screws be sterilized for a particular size of tray, but these screws will neither move nor shift about within their holders and will not come in contact with one another. This provides a very quiet autoclaving process enabling the autoclave tray to be turned or rotated without any noise of the prosthetic components or instruments coming in contact with one another or banging against their respective holders. This particular design also enables the two surgical screws (or pins) which are retained in each receiving slot to remain spaced apart from one another thereby protecting the sharp and critically machined exterior edges. This particular stacked configuration is illustrated in FIG. 7 wherein two holders 32 and 32a have been placed in oblong slots 21b and 21a, respectively. Disposed and retained within each holder are four prosthetic implant screws. Due to the side elevation orientation of FIG. 7, only two of the four pins are able to be seen. It should be understood though that a comparable pair is in alignment with the pair indicated. Implant screw 45 is retained within circular areas 41 and prosthetic implant screw 46 is retained within circular areas 42.

Referring to FIG. 6, the beginning extruded shape for the various holders is illustrated. The uneven left and right edges are provided in order to denote the fact that the extrusion may be initially provided in virtually any length and thereafter cut to the desired length. This illustration is also intended to convey an understanding that the body portion 35 of extrusion 47 begins as a solid and continuous portion. Under the more typical or standard shape for holder 32, extrusion 47 is cut to a finite length and the various receiving slots and circular areas are punched into this solid body portion thus resulting in the shape and configuration illustrated in FIG. 4. What is also intended to be illustrated is that due to the machinability of the polysulfone material, it is possible to cut, punch or machine within this solid body portion virtually any shape, thus allowing extrusion 47 to be shapable for any type of instrument, implant accessory or component which may be called for.

Referring to FIG. 5, extrusion 47 is illustrated in a side elevation orientation. This enlarged detail is provided in order to provide a better understanding of the precise geometry required for holder 32 (which begins as extrusion 47). As has been found, each of the various portions and notches have a precise and important geometry and dimensional relationship relative to the remaining portions of the extrusion. In the exemplary embodiment, base portion 33 is rectangular in shape having a lateral dimension of 0.50 inches and a vertical height of 0.10 inches. Connecting portion 36 which is symmetrical with regard to base portion 33 and body portion 35 has a lateral dimension of between 0.17 and 0.187 inches. As is intended to be illustrated, body portion 35 is acutally configured into two regions, a lower triangular region or base 49 and an upper, slightly tapered region 50. The lateral width of the undersurface of the triangular base 49, denoted as surface 51, measures 0.25 inches and the width of the base of the point it joins to the upper region 50 measures 0.187 inches. Under region 50 has a 1.5 degree taper on each side and terminates at its upper extreme with a full radius. This arrangement of an upper region which is slightly tapered and a much more noticeable tapered triangular base region assists not only in the secure retention of the holder into its corresponding oblong slot, but facilitates the security of the holder in place preventing its removal by pushing downwardly on the upper region. As previously explained, any downward force simply tneds to expand outwardly the width of the triangular region thereby actually increasing the abutment area and thus the interference of surface 51 against top surface 23. Triangular region 49 measures 0.20 inches between surface 51 and the point at which it joins to the upper region 50. Upper region 50 has an axial height of 0.80 inches, and the entire extrusion is symmetrical about centerline 52.

The polysulfone material used for extrusion 47 has a durometer of approximately 70 and a range of material properties, all of which are suitable for the disclosed use. Polysulfone is a synthetic thermoplastic polymer having a tensile strength of approximately 10,000 psi, specific gravity of 1.24 and flexural strength of approximately 15,000 psi. The material displays minimum creep and has a low expansion coefficient. These particular properties allow the material to be of suitable strength and durability for the intended purpose as well as remaining in its configured and machined shape over a wide range of temperatures as well as time. Polysulfone material, while soluble in certain aromatic hydrocarbons, is resistant to corrosive acid and alkalies as well as to heat, oxidation, detergents, oils and alcohols. The material is dimensionally stable over temperature ranges from $-100$ to $+148$ degrees Centigrade. The material may be readily processed and fabricated, and the material is typically used in power tool housings, electrical equipment, automobile components, electronic parts and computer components. The use of this material as part of the present invention is believed to be not only a novel use for the material, but a use which is ideally suited due to the material properties of polysulfone.

Referring to FIG. 8, an alternative slot configuration is illustrated. Although either style of slot, those of FIGS. 1 and 2 or that of FIG. 8, may be used with the present invention, or even together as part of a single tray, these two slot styles have very different purposes, in addition to their common purpose of retaining the polysulfone holders.

The slots illustrated in FIGS. 1 and 2 serve a very desirable and important function. Since this style requires a forced insertion, and snap receipt of the holders, the holders are not removable from the tray without damaging or destroying the holder. The result is a protected assembly whereby holders cannot be removed, from one tray for use on another. There is a level of assurance that once holders are installed they will remain with the tray, thereby avoiding the situation of a partially filled tray due to lack of holders.

The slot design of FIG. 8 makes it easier to install the holders into the tray, and eliminates the need for forced insertion. This slot design also enables the holders to be removed without damage to them. Consequently, if the holder needs to be altered or modified after installation, it can be slidably removed, reworked and then slidably reinstalled. This slidable insertion eliminates the need for substantial force to insert, and since the forced insertion is done by a machine (press), this step is eliminated. One drawback, which at times is a benefit is the fact that one tray can be cannibalized for holders to be used on another tray. This may help out in an emergency, but if partially outfitted trays are not completed with replacement holders, a full complement of components and instruments cannot be provided on a single tray.

The slot design of FIG. 8 includes a narrow channel 60 and an enlarged keyhole end 61 whose width dimension is slightly greater than the width of base portion 33. As the base portion of a holder is inserted into end 61, the connecting portion 36 lines up with channel 60. The base portion is now below the tray's surface and the connecting portion slides along channel 60 as the holder is installed. Due to the flexibility of the holder provided and in part by the contour and presence of connecting portion 36, the noninserted length of the holder is manually curved as insertion begins. By this flexing and by feeding the leading end of the holder into the slot, and by sliding the holder along the length of the slot, the entire holder is easily installed regardless of this overall length.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. An autoclave tray for sterilization of surgical components and equipment, comprising:
    (a) a plurality of slotted, flexible, synthetic holders;
    (b) said holders each including a base portion, a body portion, and a connecting portion;
    (c) said connecting portion having a width narrower than said base portion and said body portion;
    (d) said body portion including means for receiving and retaining a surgical component;
    (e) a tray including a plurality of oblong slots spaced from an outer periphery of said tray each of said holders having its connecting portion positioned within one of said oblong slots thereby connecting said holders to said tray;
    (f) said oblong slots including first and second portions;
    (g) said first portion including an elongated channel having a width;
    (h) said second portion including an enlarged portion having a width greater than the width of said channel;
    (i) said connecting portion of said holders having a width substantially equal to the width of said channel;
    (j) said enlarged portion having a width greater than said base portion of said holders for permitting said base portion to pass therethrough for readily connecting and disconnecting said holders from said tray; and (k) said body portion including a lower portion having a width greater than said channel.

2. The autoclave tray of claim 1, wherein:
(a) said plurality of holders are fabricated as an extruded member from polysulfone material.

3. An autoclave tray as in claim 1, wherein:
(a) said enlarged portion of said oblong slots is positioned adjacent one end of said channel.

4. The autoclave tray of claim 1, wherein:
(a) said tray includes a top surface having a plurality of steam holes formed therein.

5. The autoclave tray of claim 4, wherein:
(a) said top surface further includes component identification means.

6. The autoclave tray of claim 1, wherein:
(a) said body portion includes a clearance void communicating with a narrower-width open passage for connecting an uppermost edge of said body portion with said clearance void.

7. The autoclave tray of claim 6, wherein:
(a) said body portion further includes a second clearance void disposed in said narrower-width passage and spaced from said first clearance void for enabling said body portion to simultaneously retain two separate surgical components without contacting one another.

8. An apparatus for retaining instruments, comprising:
(a) a plurality of slotted, flexible, synthetic holders;
(b) said holders each including a base portion, a body portion, and a connecting portion;
(c) said connecting portion having a width narrower than said base portion and said body portion;
(d) said body portion including means for receiving and retaining an instrument;
(e) a tray including a plurality of oblong slots spaced from an outer periphery of said tray each of said holders having its connecting portion positioned within one of said oblong slots thereby connecting said holders to said tray;
(f) said oblong slots including first and second portions;
(g) said first portion including an elongated channel having a width;
(h) said second portion including an enlarged portion having a width greater than the width of said channel;
(i) said connecting portion of said holders having a width substantially equal to the width of said channel;
(j) said enlarged portion having a width greater than said base portion of said holders for permitting said base portion to pass therethrough for readily connecting and disconnecting said holders from said tray; and
(k) said body portion including a lower portion having a width greater than said channel.

9. An apparatus as in claim 8, wherein:
(a) said base portion is positioned below said tray and includes generally rectangular lateral and longitudinal cross-sections;
(b) said lower portion of said body portion is tapered; and
(c) said base portion, body portion, and connecting portion together form two laterally extending notches for receiving opposite edges of said tray defining said channel.

10. The apparatus of claim 8, wherein:
(a) said holders are fabricated as an extruded member from polysulfone material.

11. The apparatus of claim 8, wherein:
(a) said tray includes a top surface having component identification means formed thereon.

12. The apparatus of claim 8, wherein:
(a) said tray includes a plurality of steam holes formed therein.

13. The apparatus of claim 8, wherein:
(a) said body portion includes a receiving slot opening at a top end of said body portion and extending inwardly toward said lower portion for receiving therein an instrument.

14. The apparatus of claim 13, wherein:
(a) said body portion includes a second receiving slot opening at the top end of said body portion and extending inwardly towards said lower portion; and
(b) said first and second receiving slots are similarly configured and include a clearance area communicating with a narrow connecting channel.

15. The apparatus as in claim 14, wherein:
(a) said lower portion of said body portions diverges towards said base portion and has a maximum width substantially equal to one-half of the width of said base portion.

16. A method for producing an apparatus for retaining instruments, comprising the steps of:
(a) providing a plurality of slotted, flexible, synthetic holders, said holders each including a base portion, a body portion, and a connecting portion, said connecting portion having a width narrower than said base portion and said body portion, said body portion including means for receiving and retaining an instrument;
(b) providing a tray including a plurality of oblong slots spaced from an outer periphery of said tray for operably connecting said holders to said tray, said oblong slots including first and second portions, said first portion including an elongated channel having a width, said second portion including an enlarged portion having a width greater than the width of said channel, said connecting portion of said holders having a width substantially equal to the width of said channel, said enlarged portion having a width greater than said base portion, and said body portion including a lower portion having a width greater than said channel; and
(c) positioning each of said plurality of holders in a corresponding oblong slot by inserting the base portion of said holders through said enlarged portion and sliding said holder along said channel.

17. The method of claim 16, including the further step of:
(a) extruding said holders from polysulfone material for forming said base portion with generally rectangular lateral and longitudinal cross-sections, said connecting portion with generally rectangular lateral and longitudinal cross-sections and said lower portion of said body portion with a taper.

18. The method of claim 16, including the further step of:
(a) providing said body portion with a first clearance void, and a narrower-width passage for connecting said first clearance void with the top of said body portion.

19. The method of claim 18, including the further step of:
(a) providing said body portion with a second clearance void spaced from said first clearance void and in communication with said narrower-width portion.

* * * * *